US012779105B2

(12) United States Patent
Meganck et al.

(10) Patent No.: US 12,779,105 B2
(45) Date of Patent: Nov. 3, 2026

(54) FLUID MANAGEMENT SYSTEM

(71) Applicant: BOSTON SCIENTIFIC SCIMED, INC., Maple Grove, MN (US)

(72) Inventors: Jeffrey A. Meganck, N Grafton, MA (US); Leah Fanning, Clonmel (IE); John O'Donnell, Tipperary (IE); Troy Velazquez, Salem, NH (US); Damien Fitzgerald, Tipperary (IE); Linda Maher, County Kilkenny (IE); Daniela de Barba, Clonmel (IE); Peter J. Pereira, Mendon, MA (US); Niraj Prasad Rauniyar, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1137 days.

(21) Appl. No.: 17/747,744

(22) Filed: May 18, 2022

(65) Prior Publication Data

US 2022/0370706 A1 Nov. 24, 2022

Related U.S. Application Data

(60) Provisional application No. 63/190,570, filed on May 19, 2021.

(51) Int. Cl.
*A61M 3/02* (2006.01)

(52) U.S. Cl.
CPC ........ *A61M 3/0258* (2013.01); *A61M 3/0208* (2014.02); *A61M 3/0212* (2014.02);
(Continued)

(58) Field of Classification Search
CPC .............. A61M 3/0208; A61M 3/0258; A61M 3/0212; A61M 3/0216; A61M 3/022; A61M 2205/3334; A61M 2205/3331
(Continued)

(56) References Cited

U.S. PATENT DOCUMENTS

| | | | |
|---|---|---|---|
| 4,526,574 | A | 7/1985 | Pekkarinen |
| 4,650,462 | A | 3/1987 | DeSatnick et al. |

(Continued)

FOREIGN PATENT DOCUMENTS

| | | | |
|---|---|---|---|
| EP | 0329599 | A1 | 8/1989 |
| EP | 2726118 | A1 | 1/2013 |

(Continued)

OTHER PUBLICATIONS

International Search Report and Written Opinion dated Oct. 10, 2022 for International Application No. PCT/US2022/029876.

(Continued)

*Primary Examiner* — Philip E Stimpert
(74) *Attorney, Agent, or Firm* — Seager, Tufte & Wickhem, LLP

(57) ABSTRACT

A fluid management system may include an inflow pump providing a fluid inflow to a medical device, at least one pressure sensor, and a controller configured to receive pressure signals from the at least one pressure sensor, the pressure signals corresponding to a system pressure within the fluid management system. The controller may be configured to detect which one of a plurality of medical devices is fluidly connected to the inflow pump based on the pressure signals from the at least one pressure sensor and an rpm of the inflow pump.

20 Claims, 10 Drawing Sheets

(52) U.S. Cl.
CPC .......... *A61M 3/0216* (2014.02); *A61M 3/022* (2014.02); *A61M 2205/3334* (2013.01)

(58) Field of Classification Search
USPC ...................................................... 604/30, 31
See application file for complete search history.

(56) References Cited

U.S. PATENT DOCUMENTS

| | | | |
|---|---|---|---|
| 4,998,914 | A | 3/1991 | Wiest et al. |
| 5,460,490 | A | 10/1995 | Carr et al. |
| 5,464,391 | A | 11/1995 | Devale |
| 5,630,798 | A | 5/1997 | Beiser et al. |
| 5,685,821 | A | 11/1997 | Pike |
| 5,709,670 | A | 1/1998 | Vancaillie et al. |
| 5,800,383 | A | 9/1998 | Chandler et al. |
| 5,810,770 | A | 9/1998 | Chin et al. |
| 5,830,180 | A | 11/1998 | Chandler et al. |
| 5,882,339 | A | 3/1999 | Beiser et al. |
| 6,024,720 | A | 2/2000 | Chandler et al. |
| 6,077,246 | A | 6/2000 | Kullas et al. |
| 6,159,160 | A | 12/2000 | Hsei et al. |
| 6,595,957 | B1 | 7/2003 | Griffiths et al. |
| 6,896,664 | B2 | 5/2005 | Novak |
| 7,083,601 | B1 | 8/2006 | Cosmescu |
| 7,604,610 | B2 | 10/2009 | Shener et al. |
| 7,981,073 | B2 | 7/2011 | Möllstam et al. |
| D657,865 | S | 4/2012 | Williams |
| 8,444,592 | B2 | 5/2013 | Williams et al. |
| 8,512,326 | B2 | 8/2013 | Shadduck et al. |
| 8,597,228 | B2 | 12/2013 | Pyles et al. |
| 8,728,066 | B2 | 5/2014 | Shadduck et al. |
| 8,790,303 | B2 | 7/2014 | Williams et al. |
| 8,795,232 | B2 | 8/2014 | Visconti et al. |
| 8,974,448 | B2 | 3/2015 | Germain et al. |
| 9,084,847 | B2 | 7/2015 | Klein et al. |
| 9,233,193 | B2 | 1/2016 | Truckai et al. |
| 9,247,983 | B2 | 2/2016 | Truckai et al. |
| 9,254,142 | B2 | 2/2016 | Germain et al. |
| 9,272,086 | B2 | 3/2016 | Williams et al. |
| 9,289,110 | B2 | 3/2016 | Woolford et al. |
| 9,322,729 | B2 | 4/2016 | Heide et al. |
| 9,339,235 | B2 | 5/2016 | Rodriguez-Llorente et al. |
| 9,439,677 | B2 | 9/2016 | Germain et al. |
| 9,439,720 | B2 | 9/2016 | Germain et al. |
| 9,474,848 | B2 | 10/2016 | Williams et al. |
| 9,486,233 | B2 | 11/2016 | Bek et al. |
| 9,498,244 | B2 | 11/2016 | Orczy-Timko et al. |
| 9,549,754 | B2 | 1/2017 | Shadduck et al. |
| 9,597,149 | B2 | 3/2017 | Germain et al. |
| 9,603,990 | B2 | 3/2017 | Woolford |
| 9,636,170 | B2 | 5/2017 | Germain et al. |
| 9,737,362 | B2 | 8/2017 | Germain et al. |
| 9,743,979 | B2 | 8/2017 | Germain et al. |
| 9,770,541 | B2 | 9/2017 | Carr et al. |
| 9,827,037 | B2 | 11/2017 | Germain et al. |
| 9,839,473 | B2 | 12/2017 | Germain et al. |
| 9,889,246 | B2 | 2/2018 | Noolford |
| 9,901,665 | B2 | 2/2018 | Klein et al. |
| 9,907,563 | B2 | 3/2018 | Germain et al. |
| 9,943,639 | B2 | 4/2018 | Germain et al. |
| 9,999,466 | B2 | 6/2018 | Germain et al. |
| 10,004,556 | B2 | 6/2018 | Orczy-Timko et al. |
| 10,178,942 | B2 | 1/2019 | Germain et al. |
| 10,238,412 | B2 | 3/2019 | Bek et al. |
| 10,349,815 | B2 | 7/2019 | Germain et al. |
| 10,368,912 | B2 | 8/2019 | Truckai et al. |
| 10,441,353 | B2 | 10/2019 | Germain et al. |
| 10,499,987 | B2 | 12/2019 | Germain et al. |
| 10,518,005 | B2 | 12/2019 | Carr et al. |
| 10,531,785 | B2 | 1/2020 | Germain et al. |
| 10,531,912 | B2 | 1/2020 | Germain et al. |
| 10,603,104 | B2 | 3/2020 | Germain et al. |
| 10,667,857 | B2 | 6/2020 | Shadduck et al. |
| 10,716,584 | B2 | 7/2020 | Germain et al. |
| 10,751,451 | B2 | 8/2020 | Klein et al. |
| 10,786,619 | B2 | 9/2020 | Germain et al. |
| 2006/0047185 | A1 | 3/2006 | Shener et al. |
| 2007/0078370 | A1 | 4/2007 | Shener et al. |
| 2008/0154095 | A1 | 6/2008 | Stubkjaer et al. |
| 2010/0036313 | A1 | 2/2010 | Shener et al. |
| 2012/0191037 | A1 | 7/2012 | Patel et al. |
| 2012/0283691 | A1 | 11/2012 | Barnes et al. |
| 2013/0079702 | A1 | 3/2013 | Klein et al. |
| 2013/0172805 | A1 | 7/2013 | Truckai et al. |
| 2013/0197471 | A1 | 8/2013 | Williams et al. |
| 2013/0245599 | A1 | 9/2013 | Williams et al. |
| 2013/0253498 | A1 | 9/2013 | Germain et al. |
| 2014/0200612 | A1 | 7/2014 | Weir et al. |
| 2014/0336599 | A1 | 11/2014 | Patel et al. |
| 2015/0164404 | A1 | 6/2015 | Euliano et al. |
| 2015/0328379 | A1 | 11/2015 | Carr et al. |
| 2016/0089184 | A1 | 3/2016 | Truckai et al. |
| 2016/0151557 | A1* | 6/2016 | Woolford ............. A61B 1/0002 606/86 R |
| 2016/0346443 | A1* | 12/2016 | Woolford .............. A61M 3/022 |
| 2017/0000957 | A1 | 1/2017 | Carr et al. |
| 2017/0027637 | A1 | 2/2017 | Germain et al. |
| 2017/0056102 | A1 | 3/2017 | Germain et al. |
| 2017/0203028 | A1 | 7/2017 | Carr et al. |
| 2017/0224888 | A1* | 8/2017 | Hickey ............... A61M 3/0208 |
| 2018/0000998 | A1 | 1/2018 | Carr et al. |
| 2018/0132930 | A1 | 5/2018 | Germain et al. |
| 2018/0168667 | A1 | 6/2018 | Germain et al. |
| 2018/0207332 | A1 | 7/2018 | Reever et al. |
| 2018/0271596 | A1 | 9/2018 | Germain et al. |
| 2018/0361055 | A1 | 12/2018 | Pereira et al. |
| 2019/0175204 | A1 | 6/2019 | Bek et al. |
| 2019/0231967 | A1 | 8/2019 | Woolford |
| 2019/0321096 | A1 | 10/2019 | Germain et al. |
| 2019/0336166 | A1 | 11/2019 | Truckai et al. |
| 2020/0100836 | A1 | 4/2020 | Germain et al. |
| 2020/0121387 | A1 | 4/2020 | Germain et al. |
| 2020/0246067 | A1 | 8/2020 | Germain et al. |
| 2020/0281645 | A1 | 9/2020 | Shadduck et al. |
| 2020/0315640 | A1 | 10/2020 | Germain et al. |
| 2021/0128815 | A1* | 5/2021 | Byrne ................. A61M 3/0202 |
| 2021/0236728 | A1 | 8/2021 | Fanning et al. |
| 2021/0268182 | A1 | 9/2021 | O'Donnell et al. |

FOREIGN PATENT DOCUMENTS

| | | | |
|---|---|---|---|
| EP | 2758115 | A1 | 7/2014 |
| EP | 2405954 | B1 | 6/2017 |
| EP | 2726118 | B1 | 2/2018 |
| EP | 3305343 | A1 | 4/2018 |
| FR | 2727847 | A1 | 6/1996 |
| JP | 2009165646 | A | 7/2009 |
| WO | 2010042332 | A1 | 4/2010 |

OTHER PUBLICATIONS

International Search Report and Written Opinion, dated Apr. 8, 2021 for International Application No. PCT/US2020/065568.

International Search Report and Written Opinion dated Jun. 1, 2021 for International Application No. PCT/US2021/019949.

Invite to Pay Additional Fees dated Jul. 27, 2022 for International Application No. PCT/US2022/029876.

* cited by examiner

FLUID MANAGEMENT SYSTEM

CROSS REFERENCE TO RELATED APPLICATIONS

This application claims the benefit of and priority to U.S. Provisional Patent Application Ser. No. 63/190,570, filed on May 19, 2021, the disclosure of which is incorporated herein by reference.

TECHNICAL FIELD

The disclosure is directed to a fluid management system. More particularly, the disclosure is directed to a fluid management system and controls for the fluid management system.

BACKGROUND

Flexible ureteroscopy (fURS), gynecology, and other endoscopic procedures require the circulation of fluid for various reasons. Surgeons today deliver the fluid in various ways such as, for example, by hanging a fluid bag and using gravity to deliver the fluid, filling a syringe and manually injecting the fluid, or using a peristaltic pump to deliver fluid from a reservoir at a fixed pressure or flow rate via a fluid management system. Fluid management systems may adjust the flow rate and/or pressure at which fluid is delivered from the reservoir based on data collected from a procedural device, such as, but not limited to, an endoscope and/or the fluid management system. Of the known medical devices, systems, and methods, each has certain advantages and disadvantages. For example, existing systems may offer limited control over pressure and/or flow rate when a medical device or tool is inserted into a working channel of the endoscope. In some cases, this limited control may result in pressure gradients that exceed normal physiologic levels and thus may present risk to the patient. There is an ongoing need to provide alternative fluid management systems.

SUMMARY

In one example, a fluid management system may comprise an inflow pump providing a fluid inflow to a medical device; at least one pressure sensor; and a controller configured to receive pressure signals from the at least one pressure sensor, the pressure signals corresponding to a system pressure within the fluid management system. The controller may be configured to detect which one of a plurality of medical devices is fluidly connected to the inflow pump based on the pressure signals from the at least one pressure sensor and an rpm of the inflow pump.

In addition or alternatively to any example described herein, the controller is configured to automatically adjust one or more outputs for controlling the inflow pump based on which one of the plurality of medical devices is fluidly connected to the inflow pump.

In addition or alternatively to any example described herein, the controller includes a PID controller responsive to the one or more outputs.

In addition or alternatively to any example described herein, the controller calculates an output factor based on the rpm of the inflow pump and the system pressure.

In addition or alternatively to any example described herein, the controller compares the output factor to a set of known ranges, each known range corresponding to one of the plurality of medical devices.

In addition or alternatively to any example described herein, each known range has different corresponding outputs that are used to adjust the rpm of the inflow pump.

In addition or alternatively to any example described herein, the outputs include a proportional error ratio (Kp), an integral error ratio (Ki), a differential error ratio (Kd), and a sampling rate (SR).

In addition or alternatively to any example described herein, the controller is configured to selectively perform a flush responsive to a system pressure set point, a system pressure limit, and a medical device damage limit, wherein the flush is configured to increase the system pressure by a predetermined amount for a predetermined period of time.

In addition or alternatively to any example described herein, any portion of the predetermined amount of the flush exceeding the system pressure limit is restricted to the system pressure limit.

In addition or alternatively to any example described herein, if the controller determines the predetermined amount of the flush will exceed the system pressure limit, a notification is displayed and a flush override input is made available. Activation of the flush override input permits the controller to exceed the system pressure limit by the predetermined amount up to the medical device damage limit.

In addition or alternatively to any example described herein, any portion of the predetermined amount of the flush exceeding the medical device damage limit is restricted to the medical device damage limit.

In addition or alternatively to any example described herein, the system pressure set point, the system pressure limit, and the medical device damage limit are automatically selected based on which one of the plurality of medical devices is fluidly connected to the inflow pump.

In addition or alternatively to any example described herein, the at least one pressure sensor is positioned downstream of the inflow pump and upstream of the medical device.

In addition or alternatively to any example described herein, a fluid management system may comprise an inflow pump providing a fluid inflow to a medical device; at least one pressure sensor; and a controller configured to receive pressure signals from the at least one pressure sensor, the pressure signals corresponding to a system pressure within the fluid management system. The controller may be configured to detect which one of a plurality of medical devices is fluidly connected to the inflow pump based on the pressure signals from the at least one pressure sensor and an rpm of the inflow pump. The controller may be configured to automatically adjust one or more outputs for controlling the inflow pump based on which one of the plurality of medical devices is fluidly connected to the inflow pump. The controller may be configured to selectively perform a flush responsive to a system pressure set point, a system pressure limit, and a medical device damage limit automatically selected based on which one of the plurality of medical devices is fluidly connected to the inflow pump, wherein the flush is configured to increase the system pressure by a predetermined amount for a predetermined period of time.

In addition or alternatively to any example described herein, the at least one pressure sensor is positioned downstream of the inflow pump and upstream of the medical device.

In addition or alternatively to any example described herein, the fluid management system may further comprise a distal pressure sensor disposed at a distal end of the one of the plurality of medical devices fluidly connected to the inflow pump.

In addition or alternatively to any example described herein, the distal pressure sensor is configured to monitor in situ pressure increases caused by the flush. The controller is configured to limit the predetermined amount and/or the predetermined period of time of the flush such that in situ pressure remains below a predetermined in situ pressure limit.

In addition or alternatively to any example described herein, a fluid management system may comprise an inflow pump providing a fluid inflow to a medical device; at least one pressure sensor configured to detect a system pressure within the fluid management system downstream of the inflow pump; and a controller configured to detect which one of a plurality of medical devices is fluidly connected to the inflow pump based on the system pressure within the fluid management system and an rpm of the inflow pump. The controller may be configured to automatically adjust one or more outputs for controlling the inflow pump based on which one of the plurality of medical devices is fluidly connected to the inflow pump.

In addition or alternatively to any example described herein, the controller includes pre-loaded data curves relating the system pressure and the rpm of the inflow pump for each one of the plurality of medical devices.

In addition or alternatively to any example described herein, the controller is configured to automatically enable a flow compensation mode based on which one of the plurality of medical devices is fluidly connected to the inflow pump.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings, in which.

Figure 1:
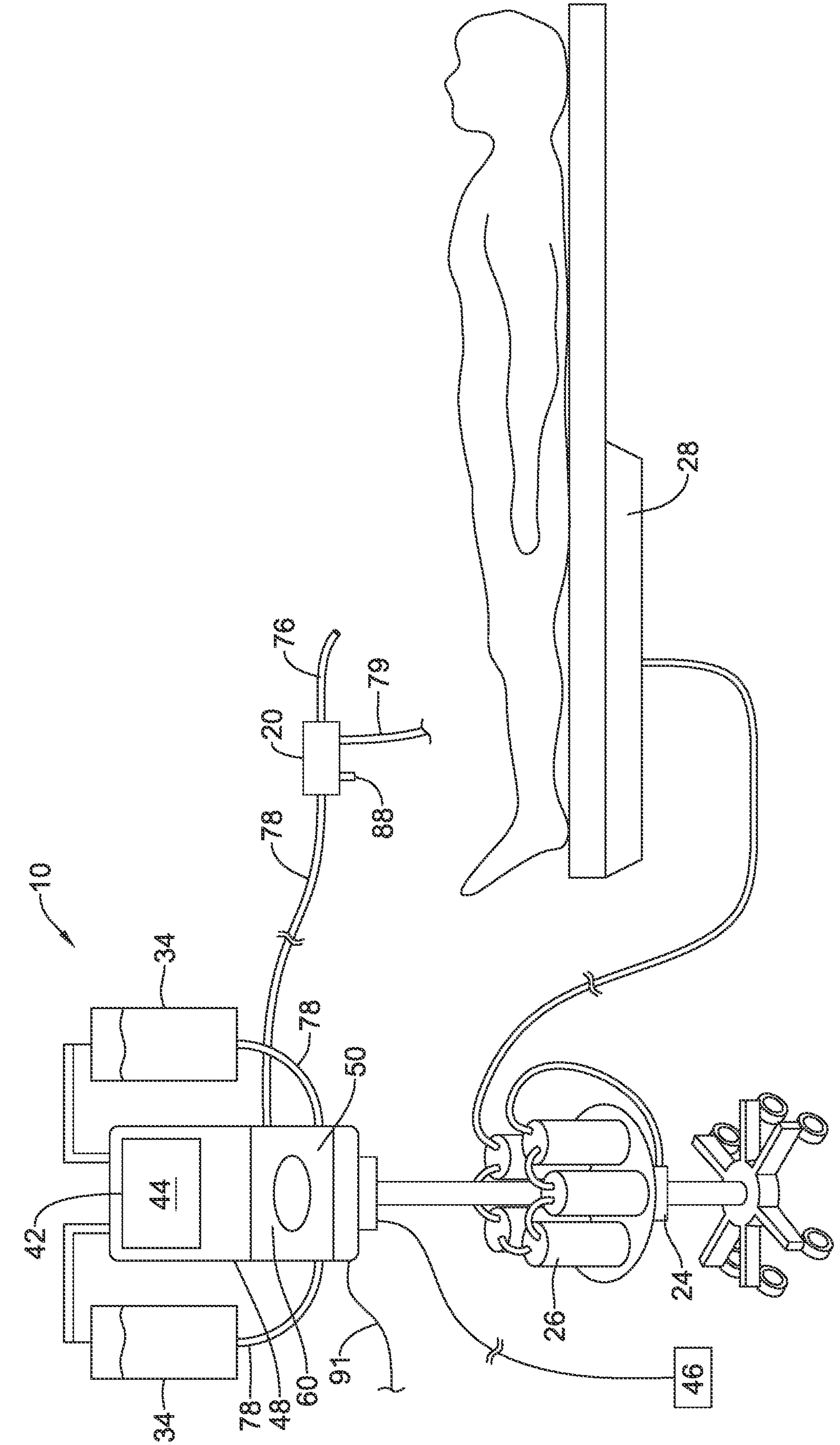
FIG. 1 is a schematic illustration of selected aspects of a fluid management system.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some fluid management systems for use in flexible ureteroscopy (fURS) procedures (e.g., ureteroscopy, percutaneous nephrolithotomy (PCNL), benign prostatic hyperplasia (BPH), transurethral resection of the prostate (TURP), etc.), gynecology, and other endoscopic procedures may attempt to regulate body cavity pressure when used in conjunction with an endoscope device using pressure and/or flow rate data from the fluid management system. During fURS procedures, the body cavity may be distended to make it easier to locate a target. In some procedures, blood and/or debris may be present in the body cavity, which may negatively affect image quality through the endoscopic device. Fluid flow (e.g., irrigation) through the endoscopic device may be used to flush the body cavity to improve image quality. In some procedures, the body cavity may be relatively small and irrigation fluid may flow continuously, which can raise intracavity fluid pressure and/or system pressure (e.g., fluid pressure within the fluid management system itself). Increased intracavity fluid pressure and/or system pressure may pose risks to the patient under some circumstances. As such, there is a need to maintain fluid flow (e.g., irrigation) into the body cavity to maintain good visualization while limiting and/or reducing intracavity fluid pressure and/or system pressure.

FIG. 1 is a schematic view of a fluid management system 10 that may be used in an endoscopic procedure, such as fURS procedures. The fluid management system 10 may be coupled to a medical device 20 that allows flow of fluid therethrough. In some embodiments, the fluid management system 10 and/or the medical device 20 may include at least one pressure sensor. In some embodiments, the medical device 20 may be an endoscope, such as a ureteroscope, a cystoscope, a nephroscope, or another scope device. In some embodiments, the medical device 20 may be a LithoVue™ scope device, or other endoscope. In some embodiments, the medical device 20 may include a temperature sensor to provide intracavity temperature feedback to the fluid management system 10, a pressure sensor to provide intracavity pressure feedback to the fluid management system 10, and/or a camera to provide visual feedback. Some specific and/or additional features of the fluid management system 10 and/or the medical device 20 shown in FIG. 1 may not be specifically referenced with respect to FIG. 1, but will be discussed below and/or in conjunction with other figures. Such features are shown in FIG. 1 for context.

Briefly, the fluid management system 10 may include an inflow pump 50 configured to pump and/or transfer fluid from a fluid supply source 34 (e.g., a fluid bag, etc.) to the medical device 20 and/or a treatment site within a patient at a fluid flow rate. In some cases, the fluid may pass through a fluid warming system 60 prior to entering the medical device 20. The flow of fluid, the pressure of the fluid, the temperature of the fluid, and/or other operational parameters may be controlled by or at least partially controlled by a controller 48. The controller 48 may be in electronic communication (e.g., wired or wireless) with the medical device 20, the inflow pump 50, and/or the fluid warming system 60 to provide control commands and/or to transfer or receive data therebetween. For example, the controller 48 may receive data from the medical device 20 such as, but not limited to, pressure signals and temperature data. The controller 48 may use the received data to control operational parameters of the inflow pump 50 and/or the fluid warming system 60.

The fluid management system 10 also includes a fluid management unit. An illustrative fluid management unit may include one or more fluid container supports, each of which supports one or more fluid supply sources 34 (e.g., one or more fluid bags). The fluid container supports may receive a variety of sizes of fluid supply sources 34 such as, but not limited to, 1 liter (L) to 5 L fluid supply sources (e.g., fluid bags). In some embodiments, the fluid management unit may be mounted to a rolling stand, which may include a plurality of wheels to facilitate easy movement of the fluid management unit when in use. However, it will be understood that the fluid supply sources 34 may also be hung at or from other locations depending on the clinical preference. The fluid container supports may extend from the rolling stand and/or the controller 48 and may include one or more hooks from which one or more fluid supply sources 34 may be suspended.

In some embodiments, the fluid management unit may include an outflow or vacuum pump 24 and a collection container 26 in fluid communication with a collection drape 28. In some embodiments, the vacuum pump 24 may include a plurality of vacuum pumps. In some embodiments, the collection container 26 may include a plurality of containers, canisters, and/or other receptacles, which may be fluidly connected to each other and/or the vacuum pump 24. In some embodiments, the collection drape 28 may include a plurality of collection drapes. The vacuum pump 24 may be operatively and/or electronically connected to the controller 48. In some embodiments, the vacuum pump 24 may be disposed adjacent to and/or near the collection container 26, as illustrated in FIG. 1. In some embodiments, the vacuum pump 24 may be disposed within the fluid management system 10. Other configurations are also contemplated.

The fluid management system 10 may also include one or more user interface components such as a touch screen interface 42. The touch screen interface 42 includes a display 44 and may include switches or knobs in addition to touch capabilities. In some embodiments, the controller 48 may include the touch screen interface 42 and/or the display 44. The touch screen interface 42 allows the user to input/adjust various functions of the fluid management system 10 such as, for example system fluid pressure, fluid temperature, or inflow pump speed (e.g., rpm) which may correlate to flow rate. The user may also configure parameters and alarms (such as, but not limited to, a system pressure limit, an inflow pump speed limit, an intracavity pressure limit, etc.), information to be displayed, etc. The touch screen interface 42 allows the user to add, change, and/or discontinue the use of various modular systems within the fluid management system 10. The touch screen interface 42 may also be used to change the fluid management system 10 between automatic and manual modes for various procedures. It is contemplated that other systems configured to receive user input may be used in place of or in addition to the touch screen interface 42.

The touch screen interface 42 may be configured to include selectable areas like buttons and/or may provide a functionality similar to physical buttons as would be understood by those skilled in the art. The display 44 may be configured to show icons related to modular systems and devices included in the fluid management system 10. The display 44 may also include a flow rate display. The flow rate display may be determined based on a desired threshold for flow rate set by the user prior to the procedure or based on known common values, etc. In some embodiments, the operating parameters may be adjusted by touching the corresponding portion of the touch screen interface 42. The touch screen interface 42 may also display visual alerts and/or audio alarms if parameters (e.g., pump speed, flow rate, pressure, temperature, etc.) are above or below predetermined thresholds and/or ranges. The touch screen interface 42 may also be configured to display any other information the user may find useful during the procedure. In some embodiments, the fluid management system 10 may also include further user interface components such as an optional foot pedal 46, a heater user interface, a fluid control interface, or other device to manually control various modular systems. For example, the optional foot pedal 46 may be used to manually control pump speed, flow rate, and/or system pressure. Some illustrative displays and other user interface components are described in described in commonly assigned U.S. Patent Application Publication No. 2018/0361055, titled AUTOMATED FLUID MANAGEMENT SYSTEM, the entire disclosure of which is hereby incorporated by reference.

The touch screen interface 42 may be operatively connected to or may be a part of the controller 48. The controller 48 may be a computer, tablet computer, or other processing device. The controller 48 may be operatively connected to one or more system components such as, for example, the inflow pump 50, the fluid warming system 60, a fluid deficit management system, etc. In some embodiments, these features may be integrated into a single unit. The controller 48 is capable of and configured to perform various functions such as calculation, control, computation, display, etc. The controller 48 is also capable of tracking and storing data pertaining to the operations of the fluid management system 10 and each component thereof. In an illustrative embodiment, the controller 48 includes wired and/or wireless network communication capabilities, such as ethernet or Wi-Fi, through which the controller 48 may be connected to, for example, a local area network. The controller 48 may also receive signals from one or more of the sensors of the fluid management system 10. In some embodiments, the controller 48 may communicate with databases for best practice suggestions and the maintenance of patient records which may be displayed to the user on the display 44.

In order to adjust the fluid flow rate or the fluid pressure through the fluid management system 10, the fluid management unit may include one or more pressurization or flow-generating devices such as the inflow pump 50. In some embodiments, the inflow pump 50 may be a peristaltic pump. In some embodiments, the inflow pump 50 may include multiple pumps or more than one pump. The inflow pump 50 may be electrically driven and may receive power from a line source such as a wall outlet, an external or internal electrical storage device such as a disposable or rechargeable battery, and/or an internal power supply. The inflow pump 50 may operate at any desired speed sufficient to deliver fluid at a target system pressure and/or at a target fluid flow rate. As noted herein, the controller 48 may be configured to automatically adjust one or more outputs for controlling the inflow pump 50. In some embodiments, the controller 48 may include a proportional-integral-derivative (PID) controller responsive to the one or more outputs for controlling the inflow pump 50. In some embodiments, the one or more outputs may include a proportional error ratio, an integral error ratio, a differential error ratio, and/or a sampling time. In some embodiments, the sampling time may be about 1 millisecond to about 100 milliseconds (ms), about 3 ms to about 90 ms, about 5 ms to about 80 ms, about 10 ms to about 60 ms, about 15 ms to about 50 ms, etc.

In some embodiments, the one or more outputs for controlling the inflow pump 50 may also be manually adjusted via, for example, the optional foot pedal 46, the touch screen interface 42, or a separate fluid controller. While not explicitly shown, the controller 48 may include a separate user interface including buttons that allow the user to increase or decrease the speed and/or the output of the inflow pump 50. In some embodiments, the fluid management system 10 may include multiple pumps having different flow capabilities. Since parameters and/or characteristics of the fluid management system 10 are generally known in advance, inflow pump speed may be correlated to flow rate within the fluid management system 10. In addition or alternatively, in some embodiments, the fluid management system 10 may include a flow rate sensor 77 (e.g., FIG. 4) to measure actual fluid flow rate. The flow rate sensor 77 may be operably connected to the controller 48 and data from the flow rate sensor 77 may be used by the controller 48 to change selected system parameters.

Inflow pump speed, fluid flow rate, and/or system pressure at any given time may be displayed on the display 44 to allow the operating room (OR) visibility for any changes. If the OR personnel notice a change in inflow pump speed, fluid flow rate, and/or system pressure that is either too high or too low, the user may manually adjust one or more outputs for controlling the inflow pump 50 and/or the inflow pump speed, fluid flow rate, and/or system pressure, back to a preferred level. In some embodiments, the fluid management system 10 and/or the controller 48 may monitor and automatically adjust one or more outputs for controlling the inflow pump 50, as discussed herein.

Figure 2:
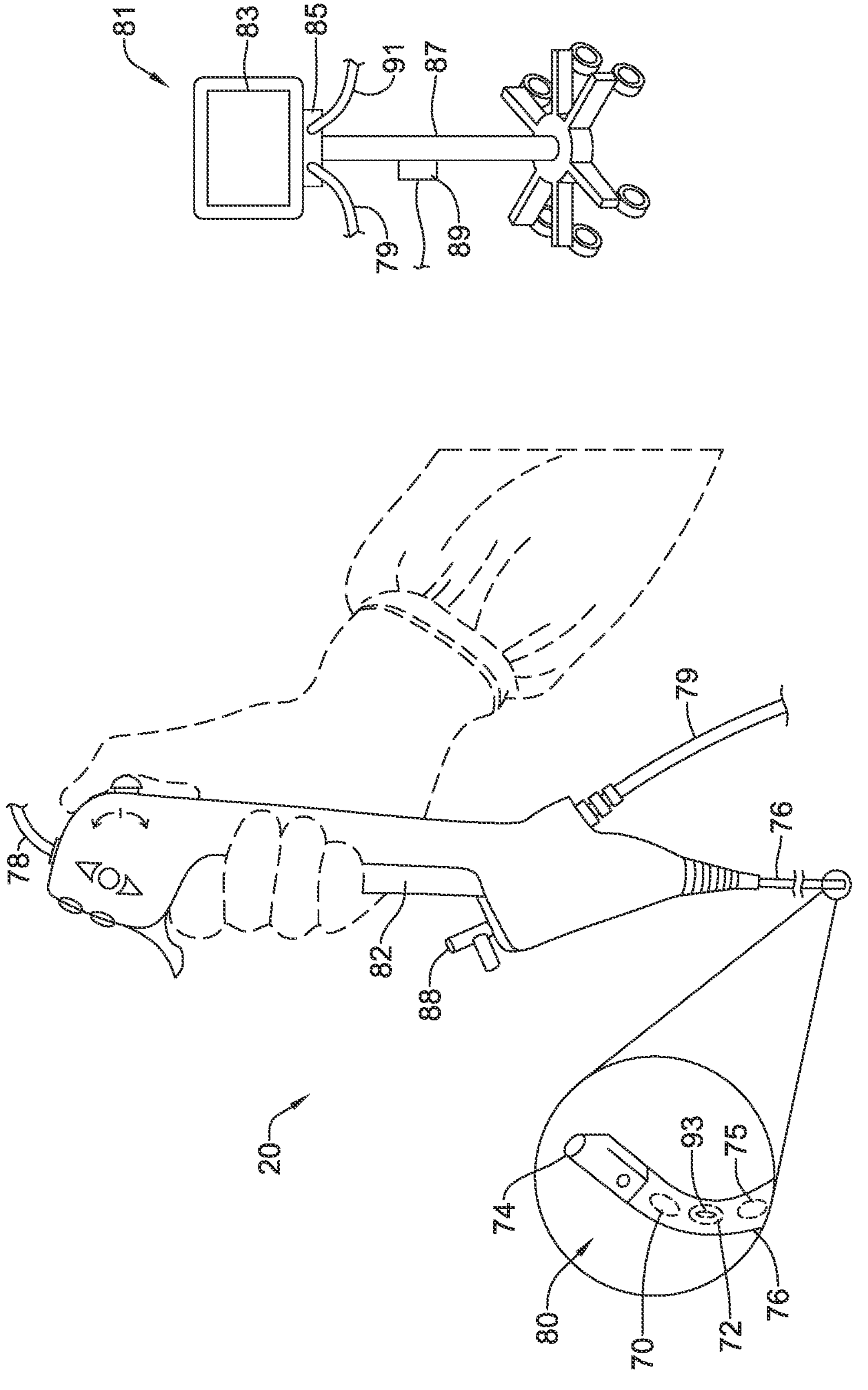
FIG. 2 illustrates selected aspects of a medical device and a workstation of the system of FIG. 1.
Figure 3:
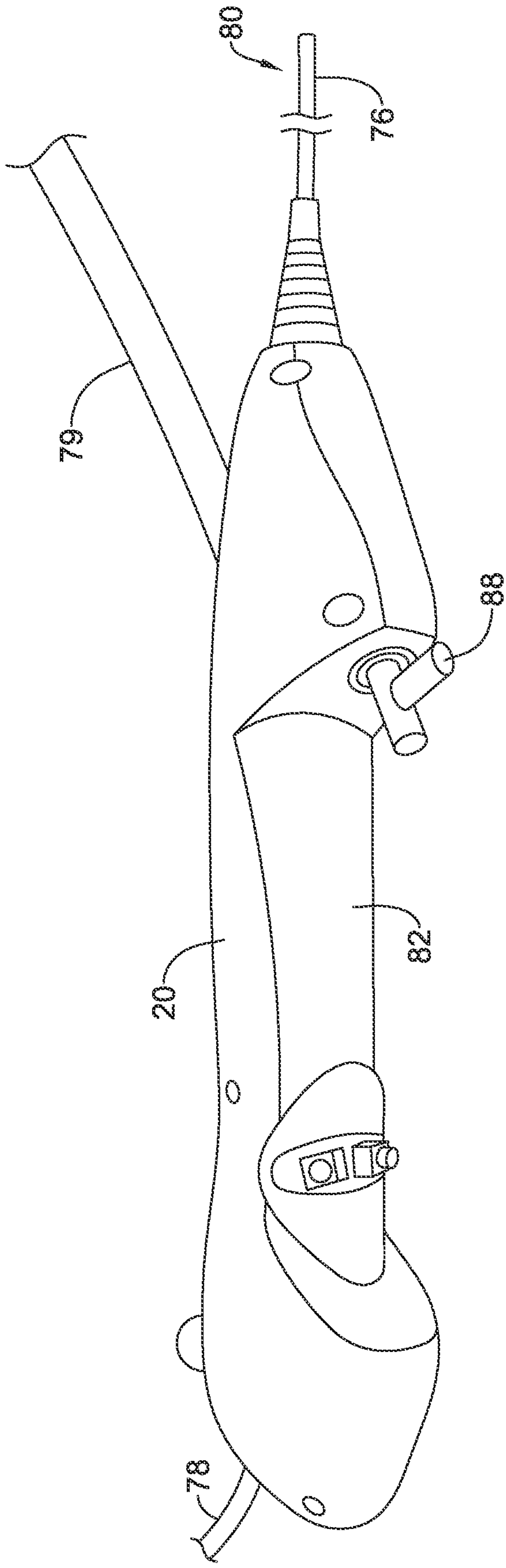
FIG. 3 illustrates selected aspects of the medical device of FIG. 2.

FIGS. 2-3 illustrate aspects of a medical device 20 that may be used in conjunction with the fluid management system 10. In some embodiments, the fluid management system 10 and/or the controller 48 may be configured to operate with and/or may be configured to detect which one of a plurality of medical devices 20 is fluidly connected to the inflow pump, as discussed herein. In some embodiments, the plurality of medical devices 20 may include one or more of an endoscope, such as a ureteroscope, a cystoscope, a nephroscope, or another scope device. Discussion which follows will refer to the medical device 20 in the singular for convenience and brevity. It shall be understood that any or all characteristics and/or configurations described with respect to the medical device 20 may apply and/or be relevant to one, some, or all of the plurality of medical devices 20.

In some embodiments, the medical device 20 may be configured to deliver fluid from the fluid management system 10 and/or the inflow pump 50 to the treatment site via an elongate shaft 76 configured to access the treatment site within the patient. In some embodiments, the inflow pump 50 may be in fluid communication with the medical device 20 and/or the elongate shaft 76. The elongate shaft 76 may include one or more working lumens for receiving a flow of fluid and/or other medical devices therethrough. The medical device 20 is connected to the fluid management system 10 via one or more supply line(s) 78 (e.g., a tube), as seen in FIG. 1 for example.

In some embodiments, the medical device 20 may be in electronic communication with a workstation 81 via a wired connection 79. The workstation 81 may include a touch panel computer 83, an interface box 85 for receiving the wired connection 79, a cart 87, and a power supply 89, among other features. In some embodiments, the interface box 85 may be configured with a wired or wireless communication connection 91 with the controller 48 of the fluid management system 10. The touch panel computer 83 may include at least a display screen and an image processor. In some embodiments, the workstation 81 may be a multi-use component (e.g., used for more than one procedure) while the medical device 20 may be a single use device, although this is not required. In some embodiments, the workstation 81 may be omitted and the medical device 20 may be electronically coupled directly to the controller 48 of the fluid management system 10.

In some embodiments, the one or more supply line(s) 78 from the fluid management system 10 to the medical device 20 may be formed of a material the helps dampen the peristaltic motion created by the inflow pump 50. In some embodiments, the supply line(s) 78 may formed from small diameter tubing less than or equal to 1⁄16 inches (1.5875 millimeters) in diameter. However, it will be understood that tubing size may vary based on the application. The supply line(s) 78 and/or the tubing may be disposable and provided sterile and ready to use. Different types of tubing may be used for various functions within the fluid management system 10. For example, one type of tubing may be used for fluid heating and fluid flow control to the medical device 20 while another type of tubing may be used for irrigation within the body and/or the treatment site.

As seen in FIG. 2, the medical device 20 may include one or more sensors proximate a distal end 80 of the elongate shaft 76. For example, the medical device 20 may include a distal pressure sensor 74 at a distal end 80 of the elongate shaft 76 to measure intracavity pressure within the treatment site. The medical device 20 may also include other sensors such as, for example, a distal temperature sensor 72, a Fiber Bragg grating optical fiber 75 to detect stresses, and/or an antenna or electromagnetic sensor 93 (e.g., a position sensor). In some embodiments, the distal end 80 of elongate shaft 76 of the medical device 20 may also include at least one camera 70 to provide a visual feed to the user on the display screen of the touch panel computer 83. In another embodiment, the medical device 20 may include two cameras 70 having different communications requirements or protocols so that different information may be relayed to the user by each camera 70. When so provided, the user may switch back and forth between cameras 70 at will through the touch screen interface 42 and/or the touch panel computer 83. While not explicitly shown, the elongate shaft 76 may include one or more working lumens for receiving the fluid and/or other medical devices.

In some embodiments, the location of the distal end 80 of the elongate shaft 76 may be tracked during use. For example, a mapping and navigation system may include an operating table (or other procedural or examination table or chair, etc.) configured to act or function as an electromagnetic generator to generate a magnetic field of a known geometry. Alternatively, or additionally, an electromagnetic generator separate from the operating table may be provided. The operating table and/or the electromagnetic generator may be coupled to a control unit which may include among other features, a processor, a memory, a display, and an input means. A position sensor (e.g., the electromagnetic sensor 93, etc.) or other antenna, may be incorporated into the distal end 80 of the elongate shaft 76 of the medical device 20. The position sensor may be configured for use in sensing a location of the position sensor in the magnetic field of the mapping and navigation system. In some embodiments, the position sensor may be electronically coupled to the workstation 81. When the position sensor is in the magnetic field, the location of the position sensor can be mathematically determined relative to the electromagnetic field source (e.g., the operating table and/or the electromagnetic generator). The workstation 81 and the control unit may communicate to determine the position of the position sensor relative to the patient.

The medical device 20 includes a handle 82 coupled to a proximal end of the elongate shaft 76. In some embodiments, the handle 82 may have a fluid flow on/off switch, which may allow the user to control when fluid is flowing through the medical device 20 and into the treatment site. The handle 82 may further include other buttons that perform other various functions. For example, in some embodiments, the handle 82 may include buttons to control the temperature of the fluid. It will be understood that while the exemplary embodiment describes a ureteroscope, the features detailed above may also be directly integrated into a cystoscope, an endoscope, a hysteroscope, or virtually any device with an image capability. In some embodiments, the medical device 20 may also include a working lumen access port 88 fluidly connected to at least one of the one or more working lumens of the medical device 20. For example, a medical instrument or tool used during a procedure may be inserted into the one or more working lumens of the medical device 20 through the working lumen access port 88.

Figure 4:
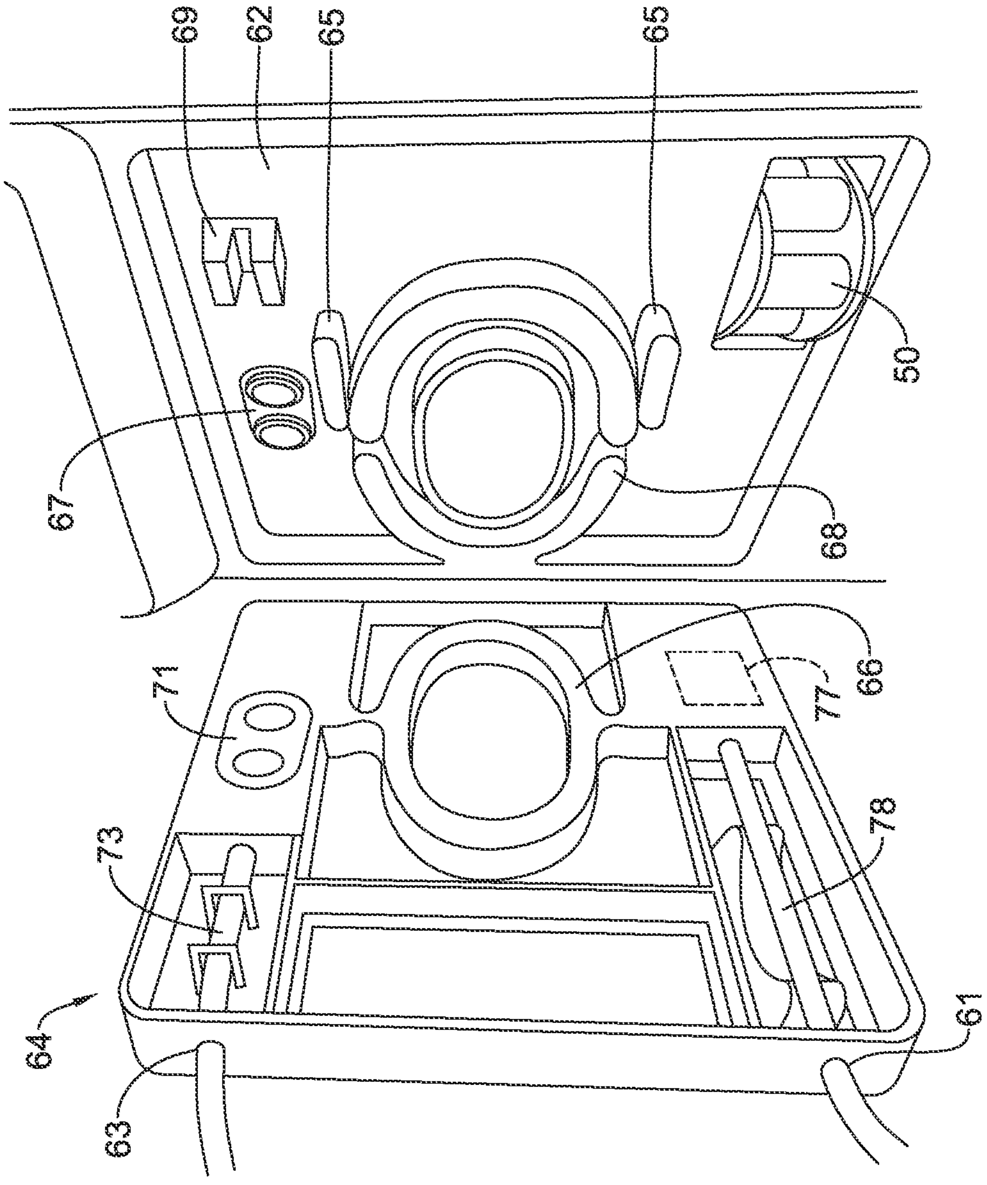
FIG. 4 is a partial perspective view illustrating selected aspects of a heater assembly and cassette of the fluid management system of FIG. 1.

In some embodiments, the fluid management system 10 may include the fluid warming system 60 for heating fluid to be delivered to the patient. The fluid warming system 60, some details of which are illustrated in FIG. 4, may include a heater 62 and a heater cassette 64. The heater cassette 64 may be configured to be a single use heater cassette 64 while the heater 62 may be reused for multiple procedures. For example, the heater cassette 64 may isolate fluid flow such that the heater 62 may be reused with minimal maintenance. The heater cassette 64 may be formed of, for example, polycarbonate or any high heat rated biocompatible plastic and is formed as a single unitary and/monolithic piece or a plurality of pieces permanently bonded to one another. In some embodiments, the heater cassette 64 may include a fluid inlet port 61 and a fluid outlet port 63 located at a lateral side of the heater cassette 64. The fluid inlet port 61 and the fluid outlet port 63 may each be configured to couple to the supply line(s) 78 of the fluid management system 10. For example, the fluid inlet port 61 may couple the fluid supply source 34 with the fluid warming system 60 (via the inflow pump 50) while the fluid outlet port 63 may couple the fluid warming system 60 with the medical device 20, each via the supply line(s) 78.

In some embodiments, the heater cassette 64 may include an internal flow path along a channel through which fluid may flow from the fluid inlet port 61 to the fluid outlet port 63. The heater cassette 64, the channel, and/or the internal flow path may include one fluid flow path or multiple fluid flow paths. In some embodiments, the channel may pass through a susceptor 66 which may allow the fluid to be heated via induction heating. When the heater cassette 64 is coupled with the heater 62, the susceptor 66 may be configured to be positioned within an induction coil 68. Other fluid warming system configurations and methods may also be used, as desired. For example, the heater 62 may include one or more heat sources such as, for example a platen system or an inline coil in the supply line(s) 78 using electrical energy. Heating may be specifically designed and tailored to the inflow pump speed, fluid flow rates, and/or system pressure required in the specific application of the fluid management system 10. Some illustrative fluid warming systems are described in described in commonly assigned U.S. Patent Application Publication No. 2018/0361055, titled AUTOMATED FLUID MANAGEMENT SYSTEM, the entire disclosure of which is hereby incorporated by reference.

While not explicitly shown, the fluid warming system 60 may include a heater user interface separate from the touch screen interface 42. The heater user interface may simply be a display screen providing a digital display of the internal temperature of the heater 62. In another embodiment, the user interface may also include temperature adjustment buttons to increase or decrease the temperature of the heater 62. In this embodiment, the heater user interface and/or the display screen may indicate the current temperature of the heater 62 as well as the target temperature to be reached. It is noted that all information output from the fluid warming system 60 may be transmitted directly to the display 44 such that no heater user interface is necessary.

The fluid warming system 60 may include one or more sensors configured to monitor the fluid flowing therethrough. For example, temperature sensors 65 may be mounted in the fluid warming system 60 such that they detect the temperature of the fluid flowing through the heater cassette 64. The temperature sensors 65 may be located at or near the fluid inlet port 61 and/or the fluid outlet port 63. In some embodiments, the temperature sensors 65 may be mounted so that they detect the temperature of fluid flowing through the heater cassette 64 prior to the fluid entering the susceptor 66 and after fluid exits the susceptor 66. In some embodiments, additional sensors may be located at a medial portion of the susceptor 66 so that they detect a progression of temperature increase of the fluid in the heater cassette 64. The temperature sensors 65 may remotely send any information to the display 44 or they may send information to heater user interface and/or the display screen thereof, if so provided. In another embodiment, the temperature sensors 65 may be hardwired with the heater user interface (if provided) which is then able to remotely transmit desired information to the display 44. Alternatively, or additionally, the temperature sensors 65 may be hardwired to and/or with the controller 48.

The heater 62 may further include at least one pressure sensor 67 configured to monitor system pressure and/or a bubble sensor 69 configured to monitor the fluid flowing through the system for bubbles. The heater cassette 64 may include a corresponding pressure sensor interface 71 and bubble sensor interface 73 that allow the at least one pressure sensor 67 and the bubble sensor 69, respectively, to monitor the fluid flowing through the heater cassette 64 when the heater cassette 64 is coupled with the fluid warming system 60. The at least one pressure sensor 67 and/or the bubble sensor 69 may remotely and/or electronically send data and/or information to the controller 48, to the display 44, and/or to the heater user interface and/or the display screen thereof, if so provided. The controller 48 may be configured to receive pressure signals from the at least one pressure sensor 67, the pressure signals corresponding to a system pressure within the fluid management system 10. In some embodiments, the at least one pressure sensor 67 and/or the bubble sensor 69 may be hardwired with the heater user interface (if provided) which is then able to remotely transmit desired information to the display 44. Alternatively, or additionally, the at least one pressure sensor 67 and/or the bubble sensor 69 may be hardwired to and/or with the controller 48.

In some embodiments, the at least one pressure sensor 67 may include one pressure sensor, two pressure sensors, three pressure sensors, or more pressure sensors. In some embodiments having two or more pressure sensors, the individual pressure sensors may be spaced apart from each other. In some embodiments, the at least one pressure sensor 67 may be positioned downstream of the inflow pump 50. In some embodiments, the at least one pressure sensor 67 may be positioned upstream of the medical device 20. In some embodiments, the at least one pressure sensor 67 may be positioned downstream of the inflow pump 50 and upstream of the medical device 20. In some embodiments, the at least one pressure sensor 67 may be configured to detect the system pressure within the fluid management system 10 downstream of the inflow pump 50.

In some embodiments, the heater cassette 64 may collectively act as a fluid reservoir. While not expressly illustrated, the fluid reservoir of the heater cassette 64 may include a pulsation dampener to reduce peristaltic pulsations, and one or more air traps to remove bubbles before and/or after heating the fluid flowing through the heater cassette 64. In some embodiments, the pulsation dampener and the one or more air traps may collectively act as the fluid reservoir. Fluid level(s) within the fluid reservoir of the heater cassette 64 may rise and fall based on a ratio between an inflow amount of fluid being pumped into the heater cassette 64 and an outflow amount of fluid exiting the heater cassette 64 (e.g., flowing to the medical device 20 and/or the patient). The outflow amount of fluid exiting the heater cassette 64 may be controlled and/or governed by the pressure gradient or difference between the fluid reservoir of the heater cassette 64 and the distal end 80 of the elongate shaft 76, and by hydraulic resistance along the flow path.

Figure 5:
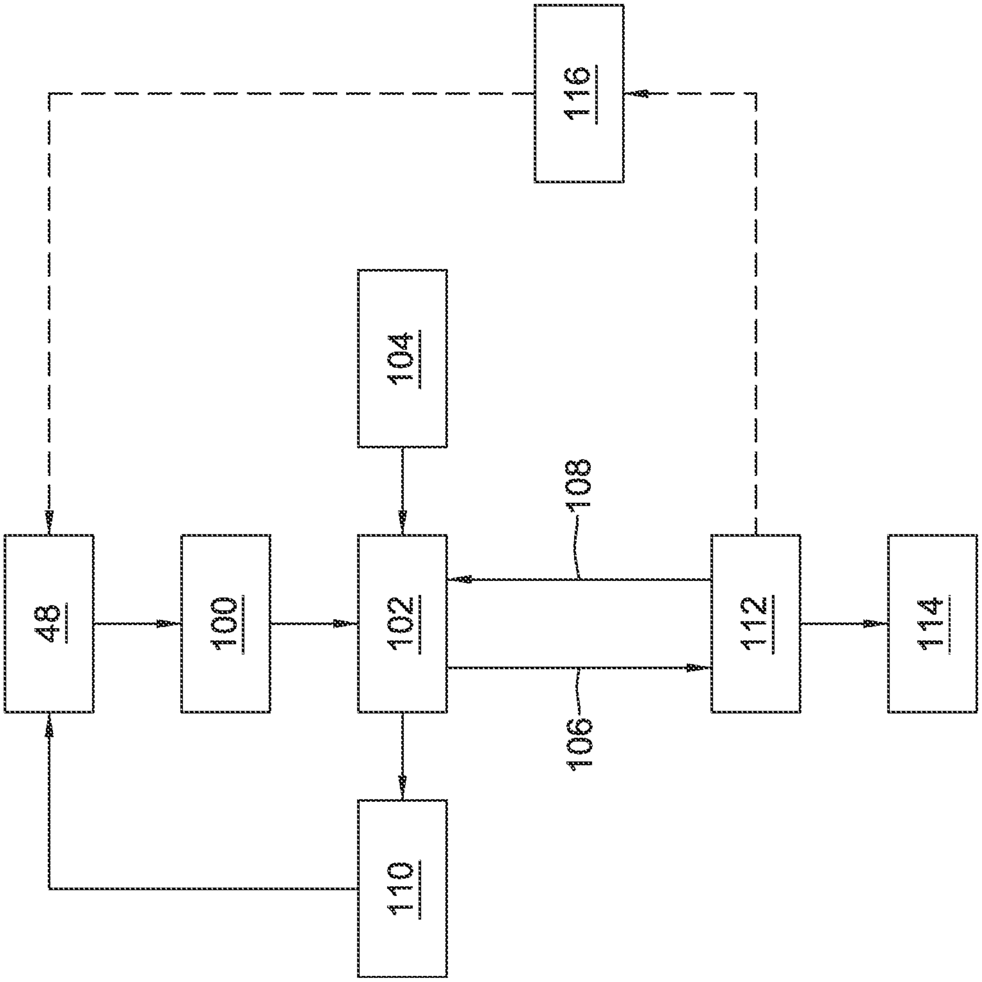
FIG. 5 illustrates control configuration(s) for the fluid management system.

In some embodiments, only system pressure is available as an input to the controller 48 (e.g., there is no distal pressure sensor 74 in the medical device 20). In such embodiments, fluid level(s) within the fluid reservoir of the heater cassette 64 is governed by the behavior shown in FIG. 5. In FIG. 5, the controller 48 sends one or more inputs to the inflow pump 50 (e.g., FIG. 1) to control inflow pump speed 100. Inflow pump speed 100 contributes to inflow of fluid into the fluid reservoir 102. The fluid reservoir 102 may have a reservoir air pressure 104 (when the fluid reservoir 102 is not full of fluid). Pressure signals and/or system pressure 110 taken by the at least one pressure sensor 67 is directed from the fluid reservoir 102 back to the controller 48, where the controller 48 evaluates the pressure signals and/or the system pressure 110 and maintains the one or more outputs to the inflow pump 50 or adjusts the one or more outputs to the inflow pump 50 as necessary to maintain desired operation. Fluid may flow (e.g., reference 106) from the fluid reservoir 102 via the one or more working lumens to the treatment site 112 (e.g., the body cavity, the ureter, the bladder, the kidney, etc.). Back pressure 108 may affect the fluid level(s) and/or pressure within the fluid reservoir 102 and thus may influence the system pressure 110. Fluid may also drain and/or outflow from the treatment site 112, which may negatively affect back pressure 108 and/or system pressure 110. This configuration of operation may be used with any applicable scope device lacking the distal pressure sensor 74 and may be termed a “standalone control configuration”. As such, in at least some embodiments, the controller 48 may be configured to operate in the standalone control configuration based on which one of the plurality of medical devices 20 is fluidly connected to the inflow pump 50 and/or in the absence of the distal pressure sensor 74 and/or a signal from the distal pressure sensor 74 of intracavity pressure.

In some embodiments, the standalone control configuration illustrated in FIG. 5 may be modified by the presence of the distal pressure sensor 74 and/or the intracavity pressure 116. As seen in FIG. 5, the intracavity pressure 116 may be sent from the treatment site 112 by the distal pressure sensor 74 to the controller 48, where the intracavity pressure 116 may be incorporated into the overall control logic. The controller 48 maintains the one or more outputs to the inflow pump 50 or adjusts the one or more outputs to the inflow pump 50 as necessary to maintain desired operation. For example, the intracavity pressure 116 from the distal pressure sensor 74 may be used to limit pressure within the treatment site by adjusting the one or more outputs to the inflow pump 50 to control the inflow pump speed 100. This configuration of operation may be used with any applicable scope device having the distal pressure sensor 74 and may be termed an “interoperable control configuration”. As such, in at least some embodiments, the controller 48 may be configured to operate in the interoperable control configuration based on which one of the plurality of medical devices 20 is fluidly connected to the inflow pump 50 and/or in the presence of the distal pressure sensor 74 and/or a signal from the distal pressure sensor 74 of the intracavity pressure 116.

In each configuration, the fluid management system 10 may operate in one of two different modes—a “pressure control mode” or a “flow compensation mode”. In the pressure control mode, the controller 48 will modulate various system parameters and/or the one or more outputs to the inflow pump 50 to keep and/or maintain the system pressure at a system pressure set point, which may be entered by the user on the touch screen interface 42. In some embodiments, the system pressure set point may be set and/or selected automatically based on which one of the plurality of medical devices 20 is fluidly connected to the inflow pump 50. As discussed herein, the system pressure may be measured by the at least one pressure sensor 67 within the fluid management unit.

In some embodiments, the fluid management system 10 may be fluidly connected to a first working lumen of the medical device 20. As such, the fluid management system 10 may be configured to control an inflow of fluid from the fluid management system 10 through the medical device 20 to the treatment site. In at least some embodiments, the first working lumen of the medical device 20 may also be used to insert a medical instrument or tool through the medical device 20 to the treatment site. Insertion of the medical instrument or tool may partially obstruct the first working lumen and thus affect the flow and/or pressure characteristics of the inflow of fluid.

Figure 6B:
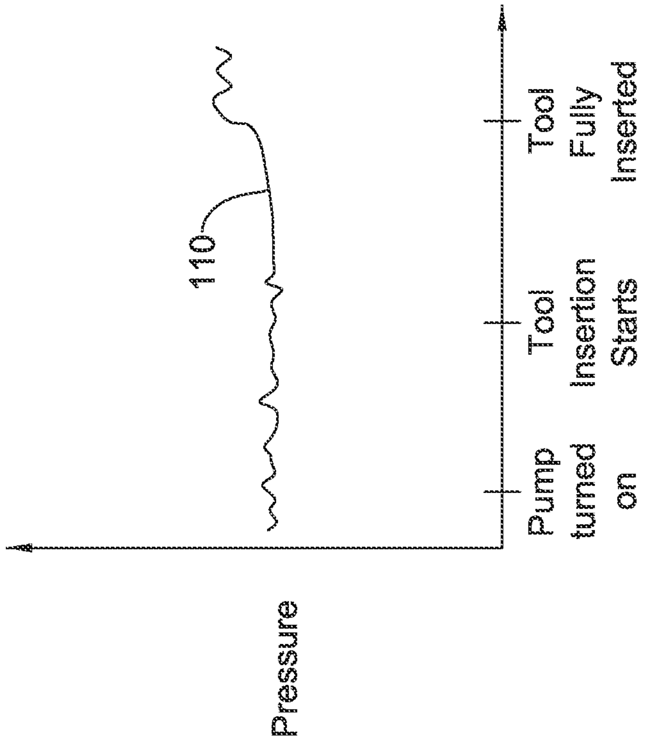
FIGS. 6A-6B illustrate characteristics within the fluid management system as a tool is inserted into the working channel of the medical device when only system pressure is available to the system.
Figure 6A:
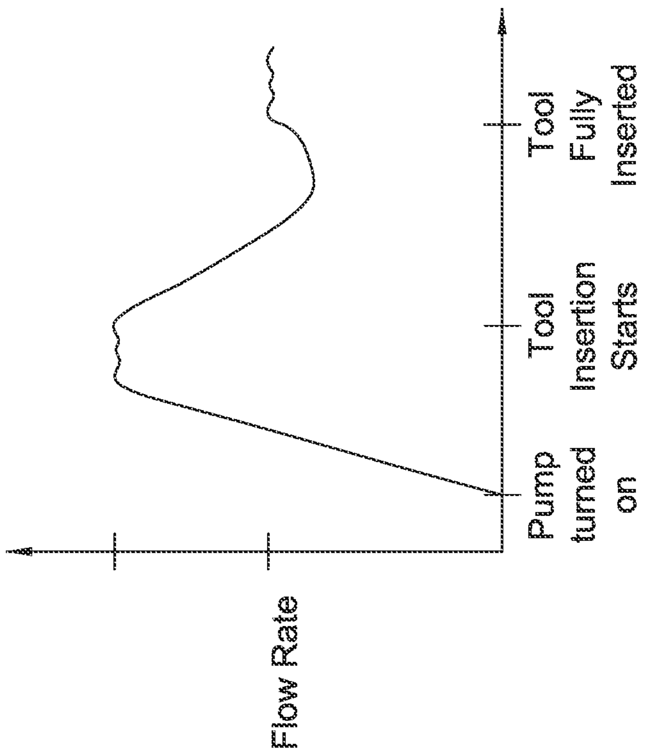

As illustrated in FIG. 6A, when the fluid management system 10 is operating in the standalone control configuration in the pressure control mode, the flow rate of inflow fluid through the first working lumen increases after the inflow pump 50 is activated. As the medical instrument or tool in inserted into the first working channel, the flow rate, which is correlated to the speed (e.g., rpm) of the inflow pump 50, will begin to decrease and stabilize once the medical instrument or tool is fully inserted. However, the flow rate of the inflow fluid will be lower than in the unobstructed first working lumen. At the same time, the system pressure 110 will be maintained and/or kept constant, as shown in FIG. 6B, by the controller 48 as pressure signals and/or the system pressure 110 is received by the controller 48. Once the medical instrument or tool is fully inserted, the system pressure 110 may increase slightly to restore at least a portion of the original flow rate, but the system pressure 100 will be limited by a system pressure limit and/or a medical device damage limit. In some embodiments, the system pressure limit and/or the medical device damage limit may be entered and/or selected by the user with the touch screen interface 42. In some embodiments, the system pressure limit and/or the medical device damage limit may be set and/or selected automatically based on which one of the plurality of medical devices 20 is fluidly connected to the inflow pump 50.

Figure 7A:
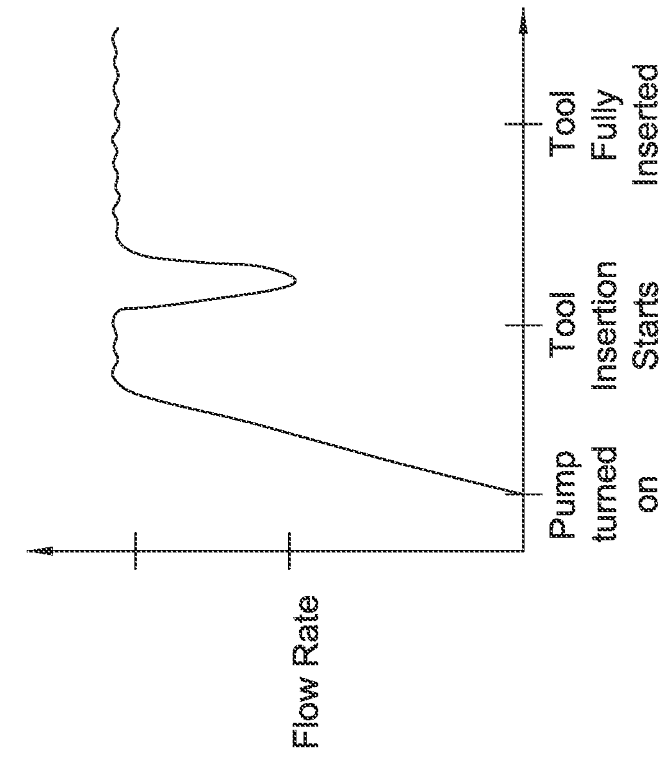
FIG. 7A-7B illustrate characteristics within the fluid management system as a tool is inserted into the working channel of the medical device when system pressure and in situ pressure are available to the system.
Figure 7B:
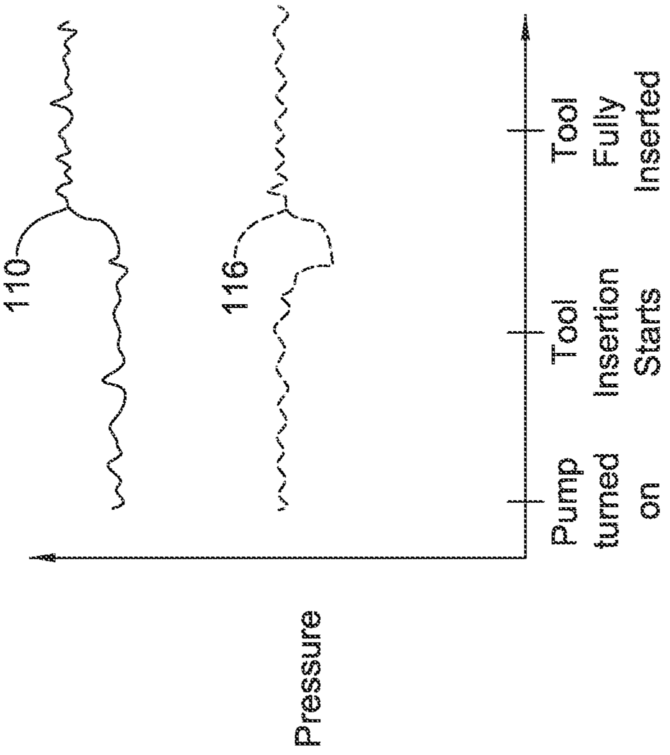

If the fluid management system 10 operates in the standalone control configuration in the flow compensation mode instead, the flow rate may be restored after the system pressure 110 increases accordingly. A response time for restoring the flow rate may be improved by incorporating the intracavity pressure 116 from the distal pressure sensor 74 where available. The intracavity pressure 116 may detect pressure drops across the fluid management system 10 (e.g., the pressure gradient) faster than the system pressure 110 alone. As such, when the fluid management system 10 is operating in the interoperable control configuration in the flow compensation mode, the system pressure 110 will simply increase when the intracavity pressure 116 drop is detected, as illustrated in FIG. 7B, and the flow rate will be restored more quickly and/or closer to its original level, as shown in FIG. 7A.

In some embodiments, when operating in the interoperable control configuration, the controller 48 may be configured to selectively perform a flush responsive to the system pressure set point, the system pressure limit, and the medical device damage limit. In at least some embodiments, the system pressure set point, the system pressure limit, and the medical device damage limit may be automatically selected based on which one of the plurality of medical devices 20 is fluidly connected to the inflow pump 50. The flush may be a separate bolus of fluid sent to the treatment site through the first working lumen of the medical device 20. In some embodiments, the flush may be sent to the treatment site through the working lumen of the medical device 20, or a different working lumen of the medical device 20. In some embodiments, the touch screen controller 42 may be used to create, activate, and/or initiate the flush on demand. In some embodiments, the optional foot pedal 46 may be used to create, activate, and/or initiate the flush on demand. In some embodiments, the flush may be configured to increase the system pressure 110 by a predetermined amount for a predetermined period of time.

FIGS. 8A-8D illustrate different configurations associated with the flush. When performing the flush, the allowable fluid pressure may be related to medical decisions made by the treating physician and/or to design limits of the equipment involved. In some embodiments, the user interface of the controller 48 may include an optional flush override that may be activated by the attending physician where and/or when the physician wants to exceed the preset and/or preselected system pressure limit.

Figure 8A:
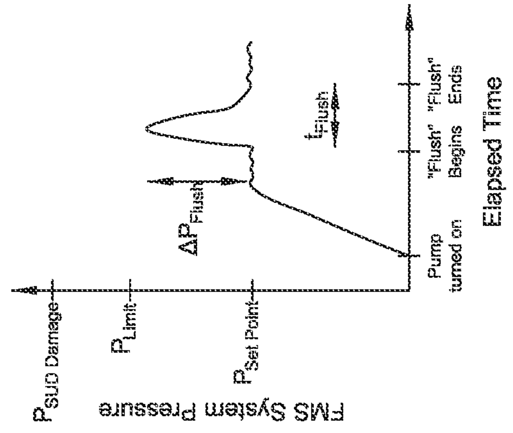
FIG. 8A-8D illustrate characteristics within the fluid management system during flush events.

FIG. 8A illustrates a case where the fluid management system 10 is operating at a system pressure set point and the flush is activated. In the case shown in FIG. 8A, the change in fluid pressure associated with the flush is less than the system pressure limit because the system pressure set point is far enough below the system pressure limit to accommodate the pressure change from the flush. As such, the flush is permitted to execute normally and fully, and no flush override is needed to activate and/or execute the flush.

Figure 8B:
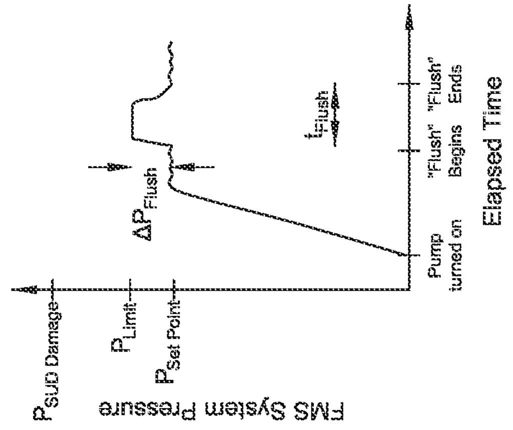

FIG. 8B illustrates a case where the fluid management system 10 is operating at a system pressure set point that is closer to the system pressure limit, wherein the pressure change associated with the flush is greater than a difference between the system pressure limit and the system pressure set point. In this case, when the flush is activated, if the controller 48 determines the predetermined amount of the flush will exceed the system pressure limit, a notification is displayed, and a flush override input is made available and/or active on the user interface. The case shown in FIG. 8B illustrates where the flush override is not selected. As such, any portion of the predetermined amount of the flush exceeding the system pressure limit is restricted to the system pressure limit. Accordingly, the flush is permitted to partially execute, up to the system pressure limit.

Figure 8C:
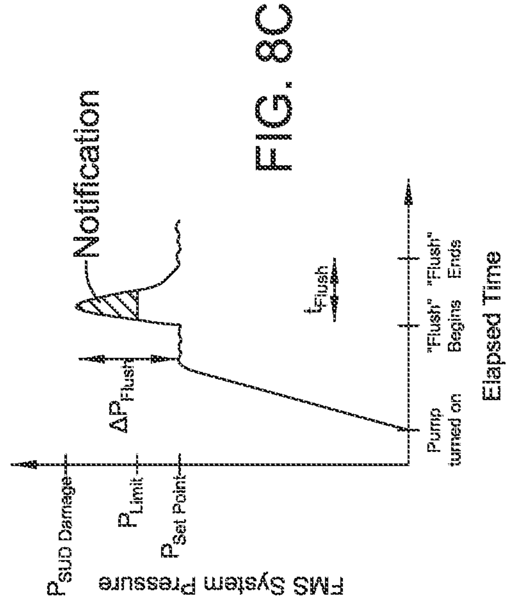

FIG. 8C illustrates a case similar to that of FIG. 8B, except that the flush override is selected and/or activated on the user interface. Notably, in the case of FIG. 8C, the pressure change associated with the flush is greater than the difference between the system pressure limit and the system pressure set point and less than a difference between the medical device damage limit and the system pressure set point. In this case, when the flush is activated, if the controller 48 determines the predetermined amount of the flush will exceed the system pressure limit, a notification is displayed, and a flush override input is made available and/or active on the user interface. Activation of the flush override input permits the controller 48 to exceed the system pressure limit by the predetermined amount up to the medical device damage limit. Since the flush override was approved, the flush is permitted to execute fully, with a notification displayed during the time the flush exceeds the system pressure limit.

Figure 8D:
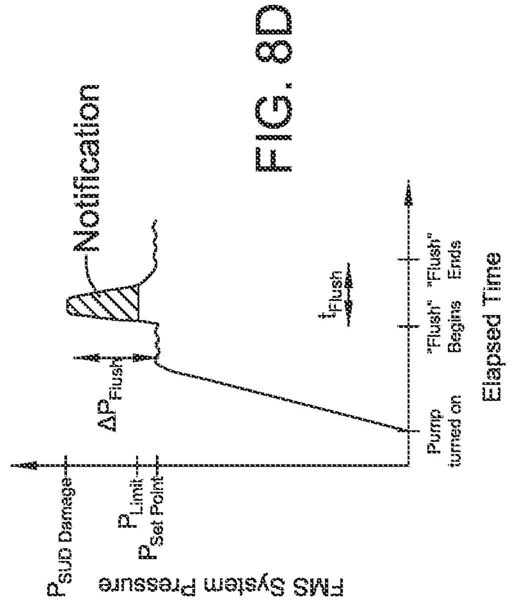

FIG. 8D illustrates a case where the pressure change associated with the flush is greater than the difference between the system pressure limit and the system pressure set point and greater than a difference between the medical device damage limit and the system pressure set point. In this case, when the flush is activated, if the controller 48 determines the predetermined amount of the flush will exceed the system pressure limit, a notification is displayed, and a flush override input is made available and/or active on the user interface. Activation of the flush override input permits the controller 48 to exceed the system pressure limit by the predetermined amount up to the medical device damage limit. Since the flush override was approved, the flush is permitted to partially execute, up to the medical device damage limit, with a notification displayed during the time the flush exceeds the system pressure limit. Any portion of the predetermined amount of the flush exceeding the medical device damage limit is restricted to the medical device damage limit.

In some embodiments, the fluid management system 10 includes the distal pressure sensor 74 disposed at the distal end 80 of the medical device 20, as discussed herein. In some embodiments, the distal pressure sensor 74 may be configured to monitor in situ pressure increases caused by the flush. The controller 48 may be configured to limit the predetermined amount and/or the predetermined period of time of the flush such that in situ pressure remains below a predetermined in situ pressure limit. In at least some embodiments, the in-situ pressure limit may be set by the user and/or attending physician using the user interface and/or the touch screen interface 42.

Figure 9:
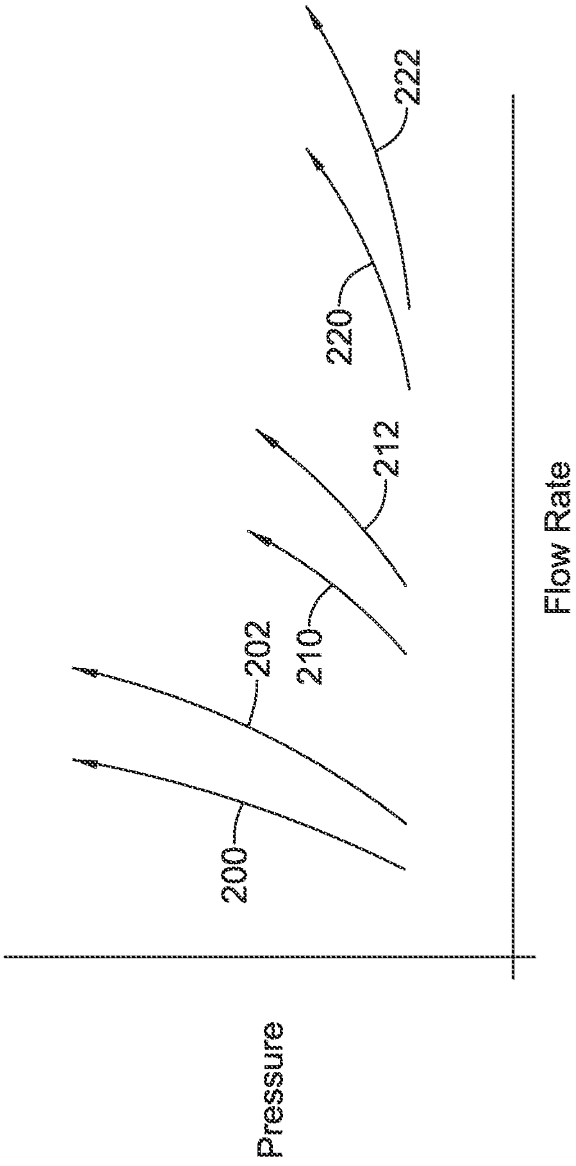
FIG. 9 is a graph illustrating pressure versus flow rate characteristics of selected combinations of medical devices and/or tools.

It will be appreciated that for both the standalone control configuration and the interoperable control configuration, the relationships between pressure and flow rate may change significantly over a range of different medical devices that are and/or will be supported by the fluid management system 10. For example, FIG. 9 illustrates data curves relating the system pressure and flow rate (which correlates to the rpm of the inflow pump 50, and which data points may be interchanged with flow rate for the purpose of establishing the data curves) for each one of the plurality of medical devices 20. It will also be appreciated that while FIG. 9 shows data curves for three different medical devices, additional data curves may be included in and/or used by the controller 48. In some embodiments, the plurality of medical devices 20 may include different types of medical devices, different sizes of medical devices, and/or different brands or manufacturers of medical devices of a single type. Other configurations are also contemplated.

FIG. 9 illustrates data curves for a first medical device with an empty and/or unobstructed working lumen at reference number 200 and the first medical device with a medical instrument or tool disposed within the working lumen at reference number 202, a second medical device with an empty and/or unobstructed working lumen at reference number 210 and the second medical device with a medical instrument or tool disposed within the working lumen at reference number 212, and a third medical device with an empty and/or unobstructed working lumen at reference number 220 and the third medical device with a medical instrument or tool disposed within the working lumen at reference number 222. The data curves may be known and/or based on bench testing data. As may be seen in FIG. 9, each medical device 20 and/or medical device 20 plus medical instrument or tool creates and/or defines a different relationship and/or line on the graph. These data curves may be pre-loaded into the controller 48. Using these pre-loaded data curves, the controller 48 may be configured to detect which one of the plurality of medical devices 20 is fluidly connected to the inflow pump 50 based on the system pressure within the fluid management system 10 and the rpm of the inflow pump 50. The controller 48 may be configured to compare current and/or actual system pressure and inflow pump speed (e.g., flow rate) data to the known and/or pre-loaded data curves for system pressure and inflow pump speed (e.g., flow rate) for the plurality of medical devices 20 in order to detect which one of the plurality of medical devices 20 is fluidly connected to the inflow pump 50. Other configurations are also contemplated.

In some embodiments, the fixed volume of the fluid reservoir of the heater cassette 64 may not be able to accommodate the flow compensation mode for every available medical device. For example, medical devices having a larger bore working lumen may be able to achieve a high flow rate but the inflow pump 50 may be unable to sufficiently increase speed enough to achieve a higher system pressure. In some embodiments, a fuzzy logic algorithm may be utilized to facilitate switching between the pressure control mode and the flow compensation mode. In some embodiments, the controller 48 may be configured to automatically enable the flow compensation mode based on which one of the plurality of medical devices 20 is fluidly connected to the inflow pump 50.

Figure 10:
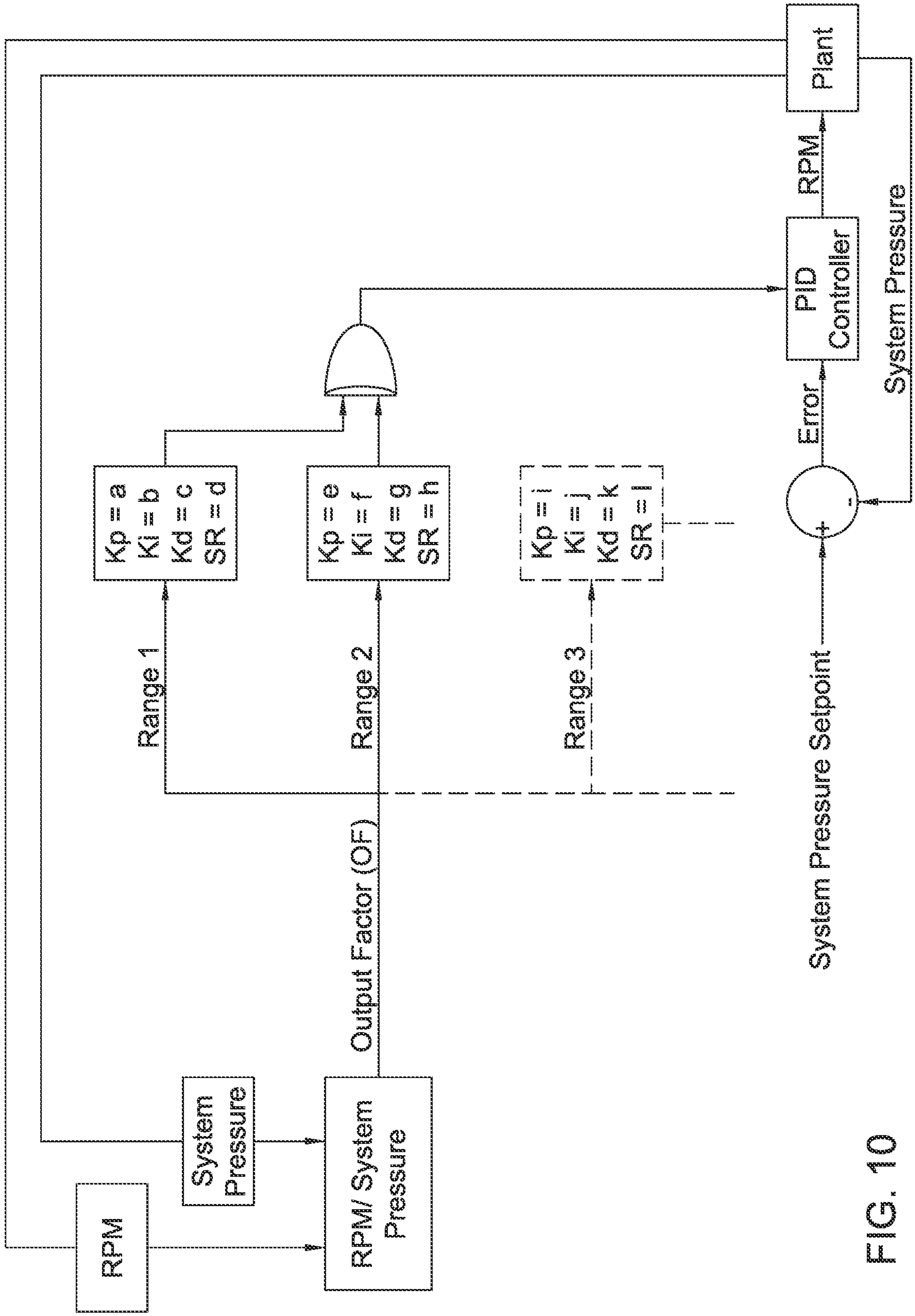
FIG. 10 illustrates exemplary fuzzy logic associated with the fluid management system.

FIG. 10 illustrates an example of the fuzzy logic algorithm that may be used by the controller 48. The controller 48 calculates an output factor (OF) as a computation of the rpm of the inflow pump 50 (or flow rate, if desired) and the system pressure. For example, the controller 48 may calculate an output factor (OF) by taking the rpm of the inflow pump 50 and dividing by the system pressure. Other configurations and/or variables are also contemplated for use in calculating the output factor (OF) including but not limited to flow rate, fluid volume in versus fluid volume out, rate of pressure change, rate of rpm change, etc.

The controller 48 then compares the output factor (OF) to a set of known ranges (e.g., Range 1, Range 2, Range 3, etc.). In one example, Range 1 may correspond to ((OF >0) and (OF<x)), Range 2 may correspond to ((OF >=x) and (OF<y)), and Range 3 may correspond to ((OF>=y) and (OF<z)). Additional ranges may be added and/or included as desired. In some embodiments, each known range (e.g., Range 1, Range 2, Range 3, etc.) may correspond to one of the plurality of medical devices 20. Each known range may define one or more outputs (e.g., Kp, Ki, Kd, SR, etc.) for controlling the inflow pump 50. In the described example, Kp corresponds to the proportional error ratio, Ki corresponds to the integral error ratio, Kd corresponds to the differential error ratio, and SR corresponds to the sampling rate. Other configurations are also contemplated. Each known range may have different corresponding values of the Kp, Ki, Kd and SR outputs (e.g., a to d, respectively, e to h, respectively, etc.) that are used to adjust parameters of the fluid management system 10 (e.g., rpm of the inflow pump 50, etc.). For instance, if the controller 48 determines the output factor is in Range 1 (and thus a first medical device type is attached to the fluid management system 10), it automatically sets the outputs to a first Kp value, a first Ki value, a first Kd value and a first SR value. If the controller 48 determines the output factor is in Range 2, (and thus a second medical device type is attached to the fluid management system 10), it automatically sets the outputs to a second Kp value, a second Ki value, a second Kd value and a second SR value. If the controller 48 determines the output factor is in Range 3, (and thus a third medical device type is attached to the fluid management system 10), it automatically sets the outputs to a third Kp value, a third Ki value, a third Kd value and a third SR value.

In some embodiments, the system pressure set point, the system pressure limit, the medical device damage limit, etc. may be automatically selected and/or set based on which one of the plurality of medical devices 20 is fluidly connected to the inflow pump 50. In some embodiments, the system pressure set point, the system pressure limit, the medical device damage limit, etc. may be associated with the set of known ranges. For example, the controller 48 may automatically select a first group of settings for the system pressure set point, the system pressure limit, the medical device damage limit, etc. when the output factor (OF) is within Range 1, and the controller 48 may automatically select a second group of settings for the system pressure set point, the system pressure limit, the medical device damage limit, etc. when the output factor (OF) is within Range 2, wherein the second group of settings is different from the first group of settings, and the controller 48 may automatically select a third group of settings for the system pressure set point, the system pressure limit, the medical device damage limit, etc. when the output factor (OF) is within Range 3, wherein the third group of settings is different from both the first and second groups of settings. Other configurations are also contemplated.

The one or more outputs (e.g., Kp, Ki, Kd, and SR) are then sent to the PID controller associated with the controller 48. The controller 48 and/or the PID controller may send inflow pump speed (e.g., rpm) data to the inflow pump 50 based on the detected range and thus the preset output values (i.e., Kp, Ki, Kd, and SR). In some embodiments, the inflow pump 50 and the at least one pressure sensor 67 may collectively be termed a "plant". As such, the inflow pump speed data may be sent to the plant by the controller 48 and/or the PID controller. Since the system pressure is at least partially dependent on inflow pump speed, the inflow pump speed (e.g., rpm) and the system pressure are fed back into the controller 48 and/or the fuzzy logic algorithm. The system pressure is also compared against the system pressure set point to determine an error differential between them, which error differential is sent to the PID controller and may be used to refine the one or more outputs if desired. In some embodiments, the fluid management system 10, the controller 48, and/or the PID controller attempts to adapt its settings to provide the fastest response time at the highest stability for changes within the system (e.g., when the medical device is inserted, withdrawn, changed, etc.).

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

The materials that can be used for the various components of the system(s) and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the fluid management system, the medical device, the elongate shaft, the inflow pump, the fluid warming system, the controller, the supply line(s), the handle, the workstation, the display screen(s), the fluid supply source(s), the collection container (s), and/or elements or components thereof.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system and/or components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system and/or components or portions thereof may be made of a material that does not substantially distort the image and create substantial artifacts (i.e., gaps in the image). Certain ferromagnetic materials, for example, may not be suitable because they may create artifacts in an MRI image. The system, or portions thereof may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the endoprosthesis and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A fluid management system, comprising:

an inflow pump providing a fluid inflow to a medical device;

at least one pressure sensor; and a controller configured to receive pressure signals from the at least one pressure sensor, the pressure signals corresponding to a system pressure within the fluid management system;

wherein the controller is configured to set a speed of the inflow pump wherein the controller is configured to detect which one of a plurality of medical devices is fluidly connected to the inflow pump based on the pressure signals from the at least one pressure sensor and the speed of the inflow pump.

2. The fluid management system of claim 1, wherein the controller is configured to automatically adjust one or more outputs for controlling the inflow pump based on which one of the plurality of medical devices is fluidly connected to the inflow pump.

3. The fluid management system of claim 2, wherein the controller includes a PID controller responsive to the one or more outputs.

4. The fluid management system of claim 1, wherein the controller calculates an output factor based on the speed of the inflow pump and the system pressure.

5. The fluid management system of claim 4, wherein the controller compares the output factor to a set of known ranges, each known range corresponding to one of the plurality of medical devices.

6. The fluid management system of claim 5, wherein each known range has different corresponding outputs that are used to adjust the speed of the inflow pump.

7. The fluid management system of claim 6, wherein the outputs include a proportional error ratio (Kp), an integral error ratio (Ki), a differential error ratio (Kd), and a sampling rate (SR).

8. The fluid management system of claim 1, wherein the controller is configured to selectively perform a flush responsive to a system pressure set point, a system pressure limit, and a medical device damage limit, wherein the flush is configured to increase the system pressure by a predetermined amount for a predetermined period of time.

9. The fluid management system of claim 8, wherein any portion of the predetermined amount of the flush exceeding the system pressure limit is restricted to the system pressure limit.

10. The fluid management system of claim 8, wherein if the controller determines the predetermined amount of the flush will exceed the system pressure limit, a notification is displayed and a flush override input is made available;

wherein activation of the flush override input permits the controller to exceed the system pressure limit by the predetermined amount up to the medical device damage limit.

11. The fluid management system of claim 10, wherein any portion of the predetermined amount of the flush exceeding the medical device damage limit is restricted to the medical device damage limit.

12. The fluid management system of claim 8, wherein the system pressure set point, the system pressure limit, and the medical device damage limit are automatically selected based on which one of the plurality of medical devices is fluidly connected to the inflow pump.

13. The fluid management system of claim 1, wherein the at least one pressure sensor is positioned downstream of the inflow pump and upstream of the medical device.

14. A fluid management system, comprising:

an inflow pump providing a fluid inflow to a medical device;

at least one pressure sensor; and a controller configured to receive pressure signals from the at least one pressure sensor, the pressure signals corresponding to a system pressure within the fluid management system;

wherein the controller is configured to set a speed of the inflow pump wherein the controller is configured to detect which one of a plurality of medical devices is fluidly connected to the inflow pump based on the pressure signals from the at least one pressure sensor and the speed of the inflow pump;

wherein the controller is configured to automatically adjust one or more outputs for controlling the inflow pump based on which one of the plurality of medical devices is fluidly connected to the inflow pump;

wherein the controller is configured to selectively perform a flush responsive to a system pressure set point, a system pressure limit, and a medical device damage limit automatically selected based on which one of the plurality of medical devices is fluidly connected to the inflow pump, wherein the flush is configured to increase the system pressure by a predetermined amount for a predetermined period of time.

15. The fluid management system of claim 14, wherein the at least one pressure sensor is positioned downstream of the inflow pump and upstream of the medical device.

16. The fluid management system of claim 14, further comprising a distal pressure sensor disposed at a distal end of the one of the plurality of medical devices fluidly connected to the inflow pump.

17. The fluid management system of claim 16, wherein the distal pressure sensor is configured to monitor in situ pressure increases caused by the flush;

wherein the controller is configured to limit the predetermined amount and/or the predetermined period of time of the flush such that in situ pressure remains below a predetermined in situ pressure limit.

18. A fluid management system, comprising:

an inflow pump providing a fluid inflow to a medical device;

at least one pressure sensor configured to detect a system pressure within the fluid management system downstream of the inflow pump; and a controller configured to detect which one of a plurality of medical devices is fluidly connected to the inflow pump based on the system pressure within the fluid management system and the speed of the inflow pump;

wherein the controller is configured to set a speed of the inflow pump wherein the controller is configured to automatically adjust one or more outputs for controlling the inflow pump based on which one of the plurality of medical devices is fluidly connected to the inflow pump.

19. The fluid management system of claim 18, wherein the controller includes pre-loaded data curves relating the system pressure and the speed of the inflow pump for each one of the plurality of medical devices.

20. The fluid management system of claim 19, wherein the controller is configured to automatically enable a flow compensation mode based on which one of the plurality of medical devices is fluidly connected to the inflow pump.

* * * * *